(12) United States Patent
McMichael et al.

(10) Patent No.: US 8,523,818 B2
(45) Date of Patent: Sep. 3, 2013

(54) ENTERAL FEEDING ASSEMBLY WITH OBTURATOR

(75) Inventors: Donald J. McMichael, Roswell, GA (US); John A. Rotella, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 949 days.

(21) Appl. No.: 12/578,877

(22) Filed: Oct. 14, 2009

(65) Prior Publication Data

US 2010/0185155 A1   Jul. 22, 2010

Related U.S. Application Data

(60) Provisional application No. 61/145,727, filed on Jan. 19, 2009.

(51) Int. Cl.
*A61M 5/178* (2006.01)

(52) U.S. Cl.
USPC ............. 604/164.04; 604/164.01; 604/174; 604/264; 604/910

(58) Field of Classification Search
USPC .............. 604/910, 104–108, 164.01, 164.03, 604/604/164.04, 164.07, 166.01, 174, 175, 604/264, 268

See application file for complete search history.

(56) References Cited

U.S. PATENT DOCUMENTS

| | | | | |
|---|---|---|---|---|
| 5,007,900 A | * | 4/1991 | Picha et al. | 604/106 |
| 5,358,488 A | * | 10/1994 | Suriyapa | 604/103.03 |
| 2007/0016134 A1 | * | 1/2007 | Suzuki et al. | 604/104 |

* cited by examiner

*Primary Examiner* — Kevin C Sirmons
*Assistant Examiner* — Laura Schell
(74) *Attorney, Agent, or Firm* — Karl V. SiDor

(57) ABSTRACT

An enteral feeding assembly is described which includes a base and a catheter positioned through the base. A portion of the catheter extends distally away from the base, and has a retainer provided on a distal end of the catheter. The retainer includes a plurality of struts having a flexible, preformed configuration which cooperate to form at least a portion of a spherical shape with openings between the struts. A shroud is positioned over at least a proximal portion of the struts to prevent the struts from causing irritation or embedding in a body lumen. The retainer is movable between an insertion configuration and a deployed configuration. An obturator and actuator are used to move the retainer between positions. A method for inserting and removing an enteral feeding assembly is also provided.

10 Claims, 11 Drawing Sheets

ENTERAL FEEDING ASSEMBLY WITH OBTURATOR

This application claims the benefit of priority from U.S. Provisional Application No. 61/145,727, filed on Jan. 19, 2009, the contents of which are incorporated herein by reference.

FIELD OF THE INVENTION

The present invention relates to improved gastrostomy tubes.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transport catheters or tubes are frequently referred to as "gastrostomy tubes", "percutaneous gastrostomy catheters", or "PEG tubes".

As indicated above, there are a variety of instances in which it may be necessary to use a catheter, one of which is the not uncommon reaction following major surgery in which a patient's stomach function is impaired for a period of time. In spite of the need to supply or supplement the body with a certain level of nutrients and the like following surgery as well as in other instances of impaired or limited gastric functionality, an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

A problem universal to low profile and non-low profile enteral feeding devices or enteral feeding assemblies (e.g., gastrostomy tubes) is the difficulty in inserting a retainer in a body lumen to hold the enteral feeding assembly in a fixed position in the lumen. Balloons have been used, which are deflated for insertion through the stoma and then inflated to hold the enteral feeding assembly in position. While balloons have many advantages, balloon may eventually leak and deflate. Other retaining fixtures have been difficult to insert through an externally stoma, and often must be endoscopically placed by a physician, usually during a surgical procedure. These retaining fixtures are typically made of the same silicone composition used to make the enteral feeding device and are frequently molded as part of the device. The end which is inserted into a body lumen may have a Malecot tip consisting of three or four generally semicircular loops of material which radiate from the end of the tube and join at a tip. The radial loop sections can seat against the interior stomach wall so as to impede the inadvertent withdrawal of the tube. Liquid nutrient passes from the tube into the stomach through the openings between these semicircular loops. Examples of conventional devices with Malecot tips or similar expanding tips are found at, for example, U.S. Pat. No. 3,915,171 for "Gastrostomy Tube" issued to Shermeta; U.S. Pat. No. 4,315,513 for "Gastrostomy and Other Percutaneous Transport Tubes" issued to Nawash et al.; U.S. Pat. No. 4,944, 732 for "Gastrostomy Port" issued to Russo; and U.S. Pat. No. 5,484,420 for "Retention Bolsters for Percutaneous Catheters" issued to Russo. Exemplary commercial products include the Passport® Low Profile Gastrostomy Device available from Cook Medical, Inc. of Bloomington, Ind. and the Mini One™ Non-Balloon Button available from Applied Medical Technology, Inc. of Brecksville, Ohio.

A shortcoming of these devices relates to the manner of insertion and withdrawal of a catheter or tube incorporating these retaining fixtures (e.g., a gastrostomy tube) into a body lumen such as into the stomach. As generally illustrated in FIG. 1, this is typically accomplished by a surgeon who inserts a stylet 100 through the length of the tube 105 and up against the end of the Malecot tip or similar expanding tip 110 while gripping the device 115 at its base 120. Referring now to FIG. 2, as the surgeon pushes the stylet 100 and tube 105 through the abdominal wall opening, the force of the end of the stylet 100 elongates the entire device 120 from about the base 115 to the tube 105 and the Malecot tip or similar expanding tip 110, thereby stretching and/or pulling the semicircular sections into a straight, elongated configuration (or stretching and/or pulling the similar expanding tip into an elongated configuration). When so elongated, the Malecot tip (or similar expanding tip) can pass through a gastrostomy opening into the stomach. When the stylus then is withdrawn, the resiliency of the tube material pulls the elongated sections of the Malecot tip back into semicircular configuration (or allows the similar expanding tip to retract to its expanded configuration), thereby securing the end within the stomach.

In practice, both the tube and the Malecot tip or similar expanding tip stretch which require providing much greater length of the article being inserted through a gastrostomy opening. This elongation of both the tube and the Malecot tip or similar expanding tip also makes withdrawal of the device more difficult because the stylet must be inserted further into the body. This presents difficulties for smaller patients, particularly for children and babies. In addition, much greater force is required to extend both the tube and the Malecot tip or similar expanding tip. The greater travel of the stylet into the body in combination with greater force applied to the stylet creates more potential for harm if the stylet is not aligned properly on the Malecot tip or similar expanding tip, if the stylet slips off the tip or if the tip fails and separates from the tube.

Accordingly, there is a need for an enteral feeding assembly and associated insertion device(s) which permits a user or health care provider to quickly and easily insert the assembly, including the retainer, externally through the patient's stoma and into a body lumen, such as, for example, a stomach lumen. Such an assembly and retainer are desirably configured so that during insertion, the retainer has an outer diameter which is about the same as the outer diameter of the portion of the catheter which extends into the stoma. However, after insertion, it is desirable that the outer diameter of the retainer expands to hold the enteral feeding assembly in the desired position for enteral feeding. Moreover, it is desirable to have a retainer that may be expanded in a body lumen without inflation. Finally, it is desirable that any devices used to insert, expand, contract, and/or remove the retainer be simple and easy to use.

SUMMARY OF THE INVENTION

In response to the difficulties and problems discussed herein, an enteral feeding assembly is provided. The enteral feeding assembly is composed of a base which has an opening allowing access through the base. The assembly also includes a flexible catheter. The flexible catheter has a proximal end and a distal end, a longitudinal axis, width and a length. The catheter is desirably positioned through the base in communication with the opening in the base. Also, the portion of the flexible catheter extending away from the base defines the distal end of the catheter. The catheter has walls defining a catheter lumen from the opening in the base to the distal end of the catheter.

The enteral feeding assembly includes a retainer provided on the distal end of the catheter. Generally speaking, the retainer may have a shape that is a generally spherical shape although other shapes and geometries are contemplated. The retainer has a proximal end and a distal end and a longitudinal axis. The retainer also has a plurality of struts having a flexible, preformed configuration which cooperate to form at least a portion of the retainer shape about the longitudinal axis with openings between the struts. The assembly may also desirably include a flexible shroud positioned over or incorporated with at least a portion of the struts at the proximal end of the retainer to prevent the struts from causing irritation or embedding in a body lumen. In an aspect of the invention, the flexible shroud and the proximal portions of the struts may desirably be a monolithic or integrally formed structure.

The enteral feeding assembly also includes an actuator configured to fit through the opening defined by the base and to fit within the lumen of the flexible catheter. The enteral feeding assembly also includes an obturator that is configured to fit within the actuator.

The actuator and the obturator combination is configured to alternate the retainer between: (a) an insertion configuration that is generated by applying an elongating force generally along the longitudinal axis of the retainer such that the struts (and, if present, the shroud) of the retainer are substantially axially aligned with the catheter to an insertion width that is substantially the same as the catheter width and an insertion length, and (b) a deployed configuration in the absence of the elongating force in which the struts (and, if present, the shroud) of the retainer have a deployed width that is substantially greater than the width of the catheter and a deployed length that is less than insertion length. In addition, the length of the flexible catheter is not significantly altered when the retainer is alternated between such configurations.

According to the present invention, the obturator and the actuator are configured to engage the distal end of the flexible catheter so that an elongating force may be applied along the longitudinal axis of the retainer to move the retainer from a deployed configuration to an insertion configuration without significantly altering the length of the flexible catheter. In an aspect of the present invention, the obturator and the actuator are configured to engage the walls of the flexible catheter defining the catheter lumen so that an elongating force may be applied along the longitudinal axis of the retainer to move the retainer from a deployed configuration to an insertion configuration without significantly altering the length of the flexible catheter.

The present invention also encompasses a method of positioning at least a portion of an enteral feeding assembly in a body lumen. The method includes the steps of: (a) positioning the above-described enteral feeding assembly near a stoma to a body lumen; (b) inserting an actuator into the catheter of the assembly, the actuator having a plunger handle at a proximal end and a split distal end including end portions, each end portion including at least one catch thereon, the distal end tapered and configured to have a diameter smaller than a diameter of the catheter lumen; (c) moving the distal end of the actuator such that the end portions extend through the distal end of the catheter such that the catch on each end portion is positioned against a portion of the distal end of the catheter; (d) inserting an obturator having a distal end and a plunger handle on a proximal end into the actuator such that the obturator extends beyond the actuator and is positioned against at least a portion of the plurality of struts; (e) moving the obturator handle next to the actuator handle to apply an elongating force generally along the longitudinal axis of the retainer to move the retainer to the insertion configuration; (f) inserting the retainer and at least a portion of the catheter into the stoma until the retainer is positioned within the body lumen; (g) removing the obturator, thereby removing the elongating force and permitting the retainer to move to the deployed configuration within the body lumen; and (h) removing the actuator from the catheter.

The present invention further encompasses an enteral feeding assembly that includes a base, a flexible catheter and a retainer generally as described above and which further includes means for applying an elongating force along the longitudinal axis of the retainer to move the retainer from a deployed configuration to an insertion configuration without significantly altering the length of the flexible catheter. The means for moving the retainer between the insertion configuration and the deployed configuration may include an obturator and an actuator.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the phrase "operable communication" means a transmission or passage for a between two points and/or two structures for a specific purpose. In this example, operable communication would be a passage which permits gasses to pass, and may also be configured to permit objects to pass.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the terms "align," "aligned," and/or "alignment" refers to the spatial property possessed by an arrangement or position of things in a straight line.

As used herein, the terms "orientation" or "position" used interchangeably herein refer to the spatial property of a place where or way in which something is situated; for example, "the position of the hands on the clock."

As used herein, the term "about" adjacent to a stated number refers to an amount that is plus or minus ten (10) percent of the stated number.

These terms may be defined with additional language in the remaining portions of the specification.

DETAILED DESCRIPTION OF THE INVENTION

Figure 1:
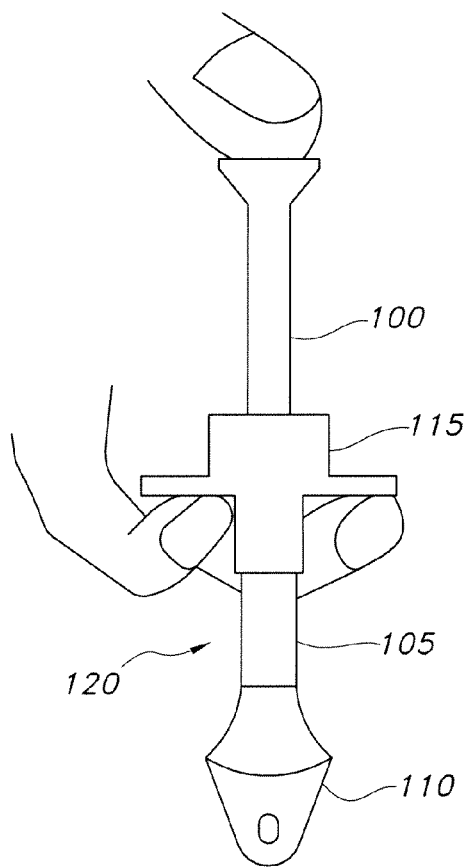
FIG. 1 is an illustration of a conventional prior art device in which a stylet is positioned in the device but force has not been applied to elongate the device.

The invention(s) disclosed herein relate generally to improved medical care for patients who require enteral feeding. More particularly, the invention(s) disclosed herein relate to an enteral feeding assembly including a retainer for holding at least a portion of the assembly in a body lumen. The invention(s) disclosed herein may also include one or more devices used to insert, expand, and/or remove at least a portion of an enteral feeding assembly from a body lumen.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Turning now to the drawings, the present invention is generally illustrated in FIGS. 3-12. An enteral feeding assembly 10 is illustrated with an obturator 12 and an actuator 14, as shown in FIGS. 3-8. The enteral feeding assembly includes a base 16 having a catheter 18 generally in the form of a tubular section. That is, the catheter has catheter walls defining a catheter lumen. The catheter may have a width which may be expressed as a diameter. The catheter also may have a length and a longitudinal axis. The catheter may have a circular cross-section or it may have other cross-sectional shapes such as square, hexagon, triangle, pentagon, oval, ellipsoid or the like.

The base is desirably, but not by way of limitation, a low-profile base configured to be positioned on a patient's skin surface and to extend over and across a stoma formed through the patient's skin surface (not shown). The catheter 18 desirably, but not by way of limitation, is coupled to or formed with the base 16, and it positioned at about a ninety (90) degree angle relative to the base 16. That is, the base 16 is aligned along a first axis such as, for example a horizontal axis and the catheter is aligned along a second axis that is generally perpendicular (oriented about ninety (90) degrees) to the base. The catheter 18 includes an open proximal end (not shown) which intersect the base 16 and an open distal end 22, each of which communicated with a catheter lumen 24 defined by the walls of the catheter and extending through the catheter 18 from the proximal end to the distal end. A retainer 25 is provided at the distal end 22 of the catheter 18.

Generally speaking, the catheter 18 may be secured to the base 16 by known techniques including adhesives, solvent welding or the like. Alternatively, the catheter 18 and the base 16 may be formed as an integral component. The retainer 25 is desirably composed of a plurality of flexible struts 26, each of which extends radially from the distal end 22 of the catheter 18. Each of the plurality of struts 26 is coupled to or formed to extend, at a proximal end 28 of each strut 26, from the distal end 22 of the catheter 18. Each of the plurality of struts 26 join together at a distal end 30 and form a junction of the plurality of struts 26, as generally illustrated in FIGS. 8-11.

It is contemplated that the plurality of struts of the retainer may be composed of a first layer or sleeve of material that defines a first set of struts and a second, slightly smaller layer or sleeve of material that defines a second set of struts and which is nested or fitted inside the first layer or sleeve. The second layer/sleeve is fitted within the first layer/sleeve with a sufficient offset so that the plurality of struts of the second layer can fill in the spaces between the plurality of struts of the first layer so that, when deployed, additional surface area and structure is provided.

Each of the plurality of struts 26 is desirably formed from a resilient material having a memory. Such a material permits an object formed from the material to remain in a preformed shape. Therefore, the object maintains this preformed shape until it is urged or forced into another shape. Suitable materials include, but are not limited to, "soft" or elastomeric medical grade silicone polymers and "soft" or elastomeric medical grade polyurethane polymers. The "soft" polymers may have a Shore A Hardness of between about 40 and about 80, more desirably between about 50 and about 70. The Shore Hardness testing of soft plastics is most commonly measured by the Shore (Durometer) test using either the Shore A or Shore D scale. The Shore A scale is used for "softer" rubbers while the Shore D scale is used for "harder" ones. The Shore A Hardness is the relative hardness of elastic materials such as rubber or soft plastics can be determined with an instrument called a Shore A Durometer. If the indenter completely penetrates the sample, a reading of 0 is obtained, and if no penetration occurs, a reading of 100 results. The reading is dimensionless.

The Shore hardness is measured with an apparatus known as a Durometer and is sometimes also referred to as Durometer Hardness. The hardness value is determined by the penetration of the Durometer indenter foot into the sample. Because of the resilience of rubbers and plastics, the hardness reading my change over time so the indentation time is sometimes reported along with the hardness number. The ASTM test number is ASTM D2240 while the analogous ISO test method is ISO 868.

The catheter 18 and the retainer 25 may be secured together or they may be formed as an integral component. It is contemplated that the base 16, the catheter 18 and the retainer 25 may be formed as an integral or monolithic component. In certain embodiments of the invention, the base 16, the catheter 18 and the retainer 25 may be formed as an integral or monolithic component. In other embodiments, the base 16, the catheter 18 and the retainer 25 may be formed separate and joined together using conventional techniques.

In the present embodiment, each strut 26 is constructed to provide a preformed shape. In this instance, each of the plurality of struts 26 is preformed to form a radially-extending arc or ach. That is, the plurality of struts 26, in the unrestrained position, extend radially outward and together form generally, a spherical shape, with openings between each of the plurality of struts 26. Of course, it is contemplated that the struts may form a non-spherical shape such as any geometric shape including, but not limited to, a cube, a conical shape, a generally flat planar shape or the like as well as various combinations thereof.

A dimple 32 is formed at the junction formed at the distal ends 30 of the plurality of struts 26, as illustrated in FIGS. 8-11. The dimple 32 is formed as a slight convexity or protuberance on an outer surface 34 of the retainer 25. The dimple 32 forms a concavity or detent 36 on an inner surface 37 of the retainer 25. In an embodiment of the invention, the plurality of struts 26 may be at least partially covered over the outer surface 34 thereof by a shroud 38. The shroud 38 may be coupled to or formed with the plurality of struts 26 at or near the proximal end 28 of the struts 26. The shroud 38 may be provided so that the struts 26 do not rub against or embed within the surface of the body lumen. In another embodiment, the shroud 38 may also be incorporated as a web or similar structure between the struts 26.

Figure 11:
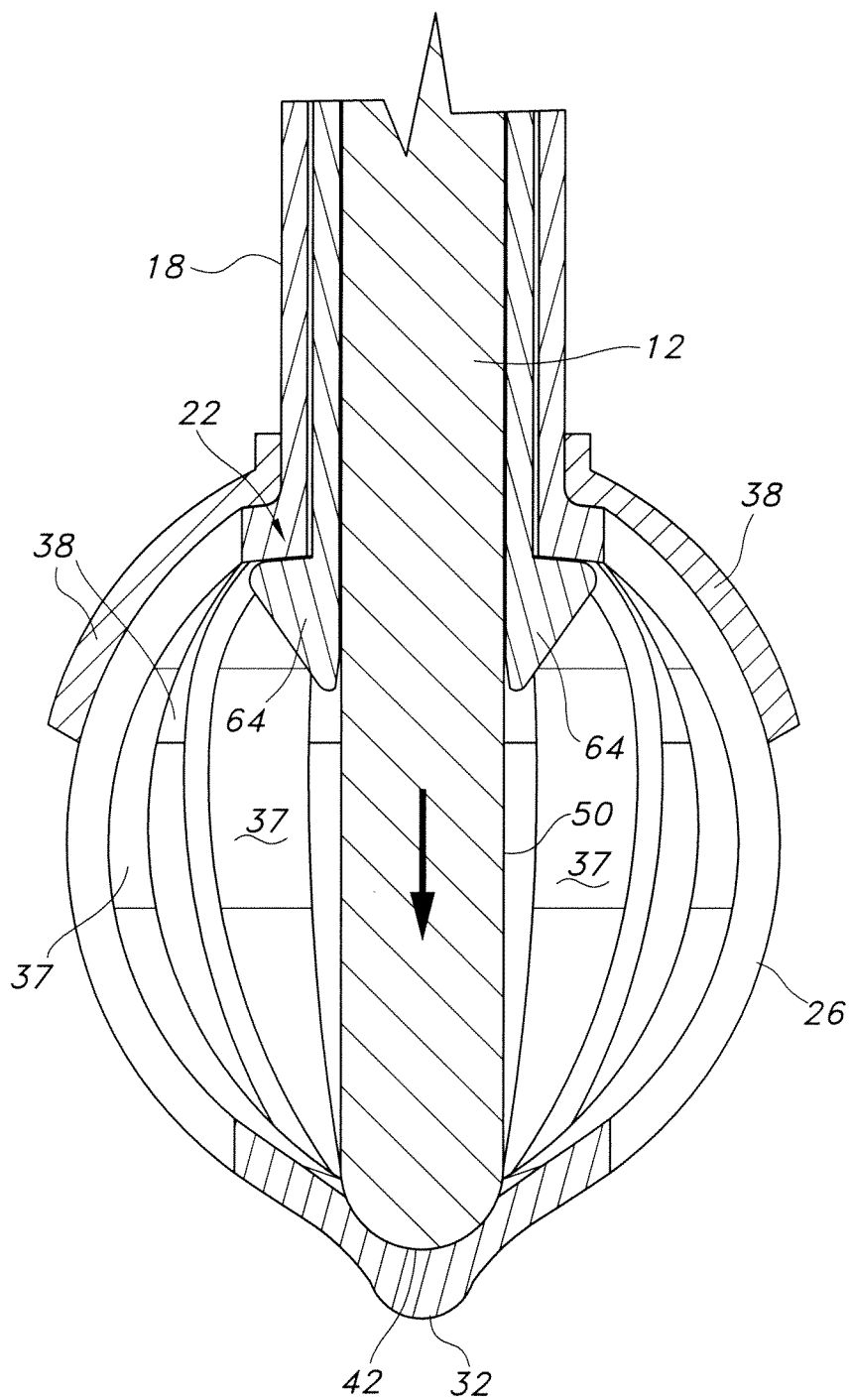
FIG. 11 is a side view of an exemplary enteral feeding assembly showing the obturator extending through the actuator such that the catches on the distal end of the actuator engage a catheter of the enteral feeding assembly and in which the obturator pushes against the distal end of the retainer to urge it into axial alignment relative to the obturator and the catheter of the enteral feeding assembly.
Figure 12:
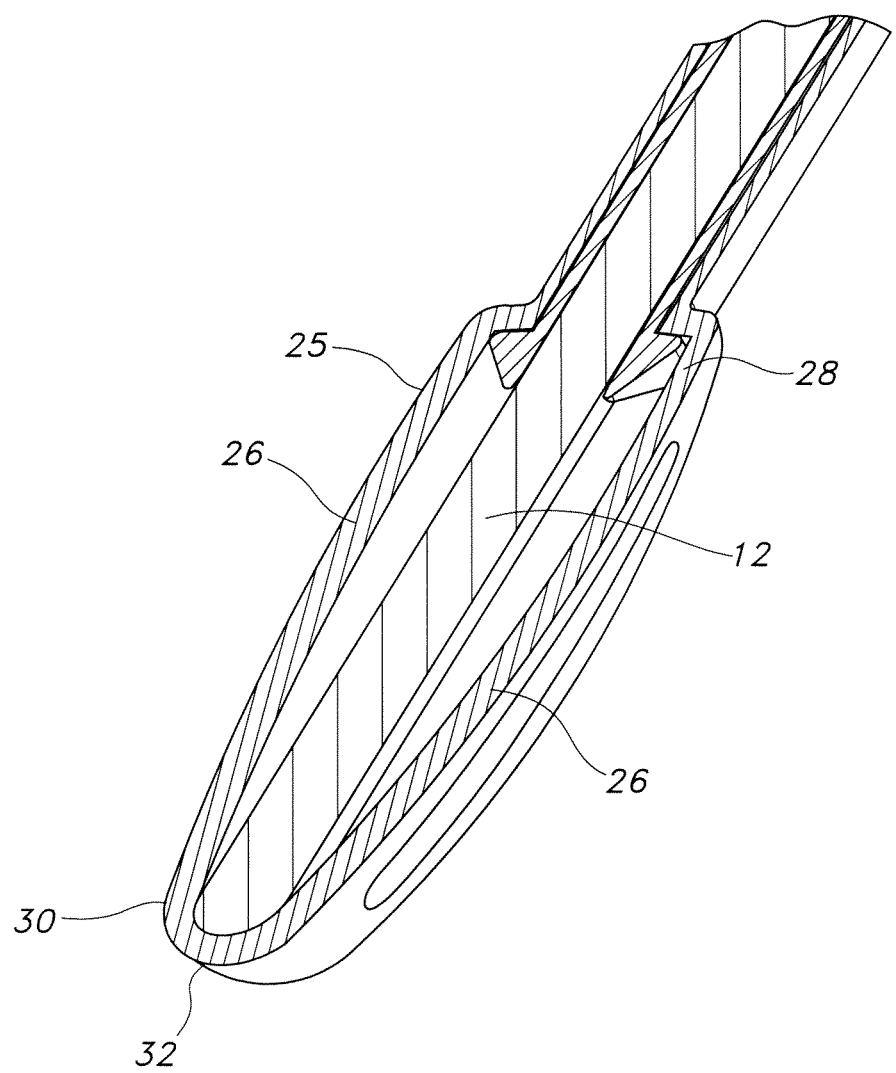
FIG. 12 is a side sectional view similar to FIG. 11, showing the obturator positioning the plurality of struts of the retainer in an axial alignment relative to the obturator and a catheter of the enteral feeding assembly.

In an insertion configuration, the plurality of struts 26 are elongated and extend axially away from the distal end 22 of the catheter 18, as shown in FIGS. 11 and 12. The plurality of struts 26 are desirably positioned in an axial alignment with the distal end 22 of the catheter 18. If a shroud 38 is employed, the shroud 38 is similarly positioned in an axial alignment with the distal end 22 as well (not shown). The shroud 38 is desirably light-weight, and may have axially positioned folds formed in the shroud 38 when positioned in the restrained position. This insertion configuration and axial alignment is desirably created by the obturator 12 and the actuator 14.

Figure 8:
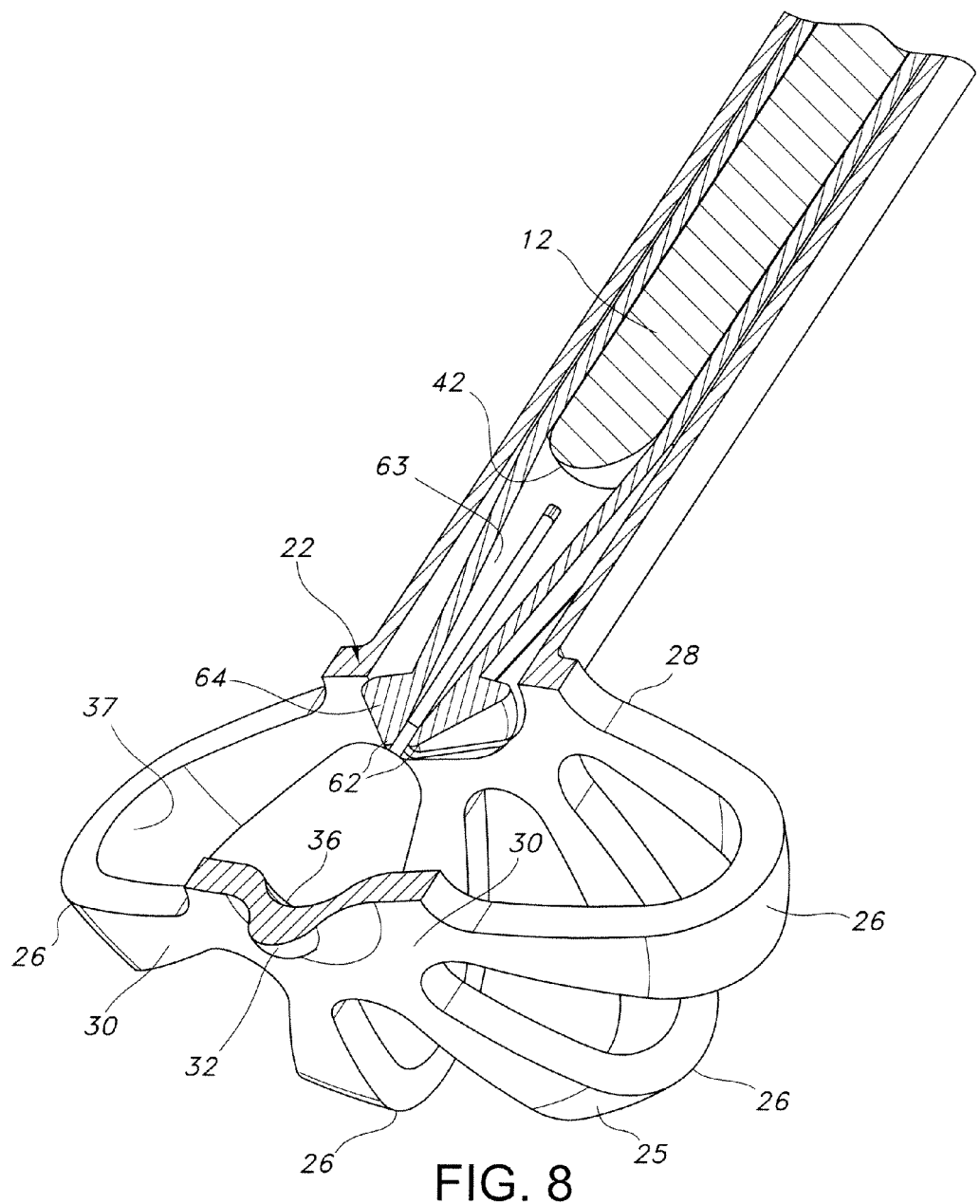
FIG. 8 is a sectional perspective view of a portion of FIG. 7 taken along lines 6-6.
Figure 8A:
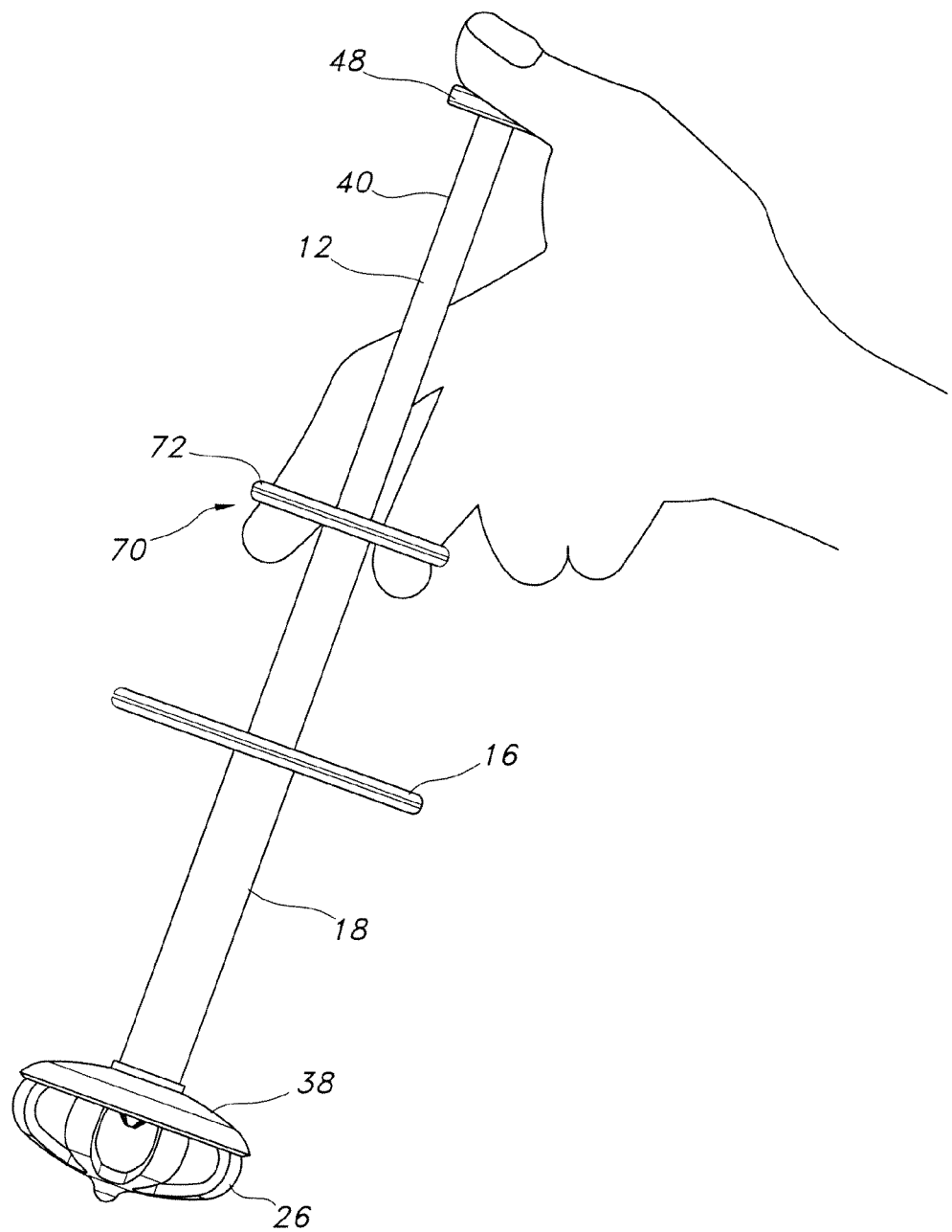
FIG. 8A is a side view showing an exemplary configuration of the enteral feeding assembly.
Figure 8B:
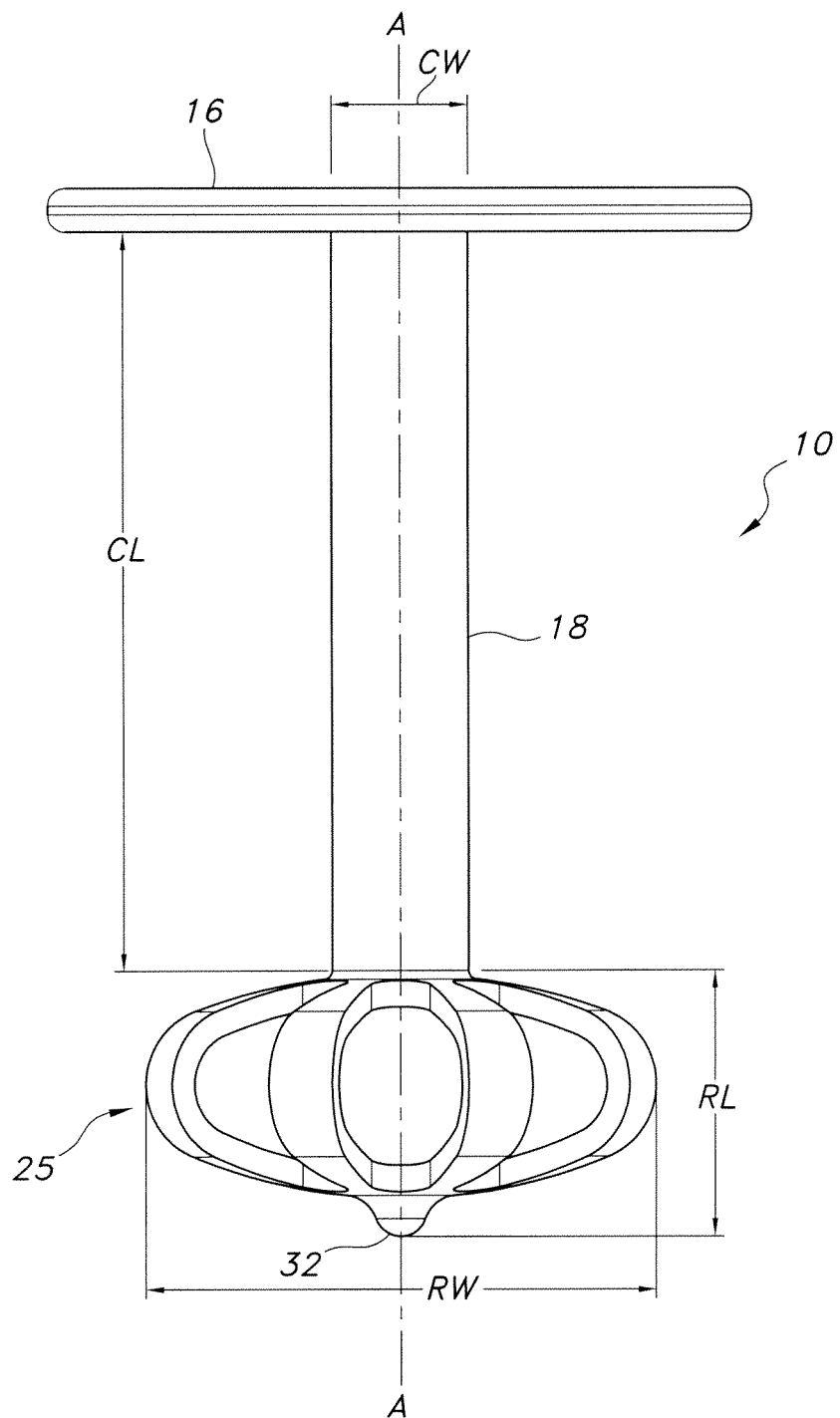
FIG. 8B is a side view showing features of an exemplary configuration of the enteral feeding assembly.

Referring briefly to FIG. 8B, there is shown a side view of the enteral feeding assembly 10 illustrating the longitudinal axis "A" of the catheter 18 and the retainer 25. The catheter 18 has a length shown as "CL" and a width shown as "CW". The retainer 25 has a length "RL" and a width "RW". Generally speaking, an elongating force is applied along the longitudinal axis "A" to only the retainer 25 such that the retainer length "RL" increases and the retainer width "RW" decreases such that the retainer 25 achieved its insertion configuration as generally illustrated in FIGS. 11 and 12 whereby the retainer width "RW" is substantially similar to the catheter width "CW" without significantly increasing the length of the catheter "CL".

Figure 5:
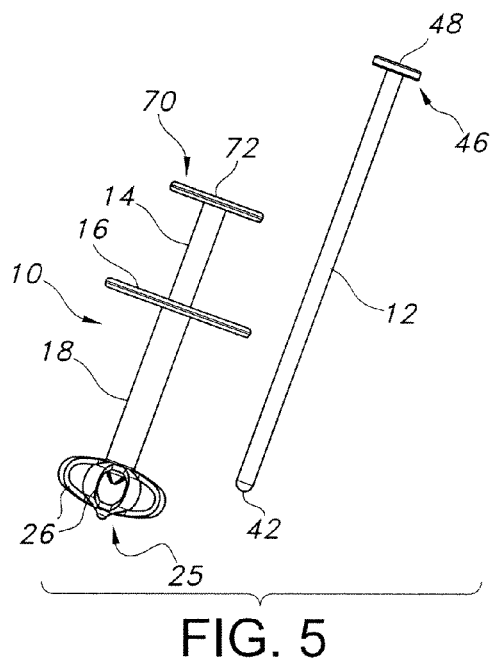
FIG. 5 is a side view of an exemplary enteral feeding assembly of FIG. 3, showing the actuator positioned in the enteral feeding assembly and the obturator positioned separately beside the enteral feeding assembly.
Figure 4:
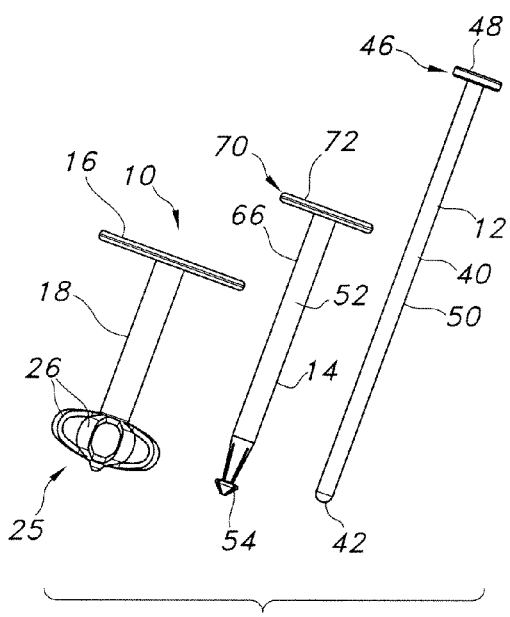
FIG. 4 is a side view of an exemplary enteral feeding assembly of FIG. 3, showing the obturator and actuator positioned separately beside the enteral feeding assembly.
Figure 6:
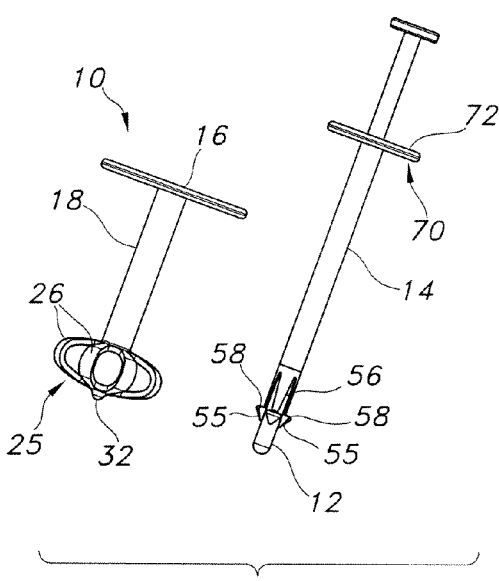
FIG. 6 is a side view of an exemplary enteral feeding assembly of FIG. 3, showing the enteral feeding assembly and showing separately the obturator disposed through the actuator.
Figure 7:
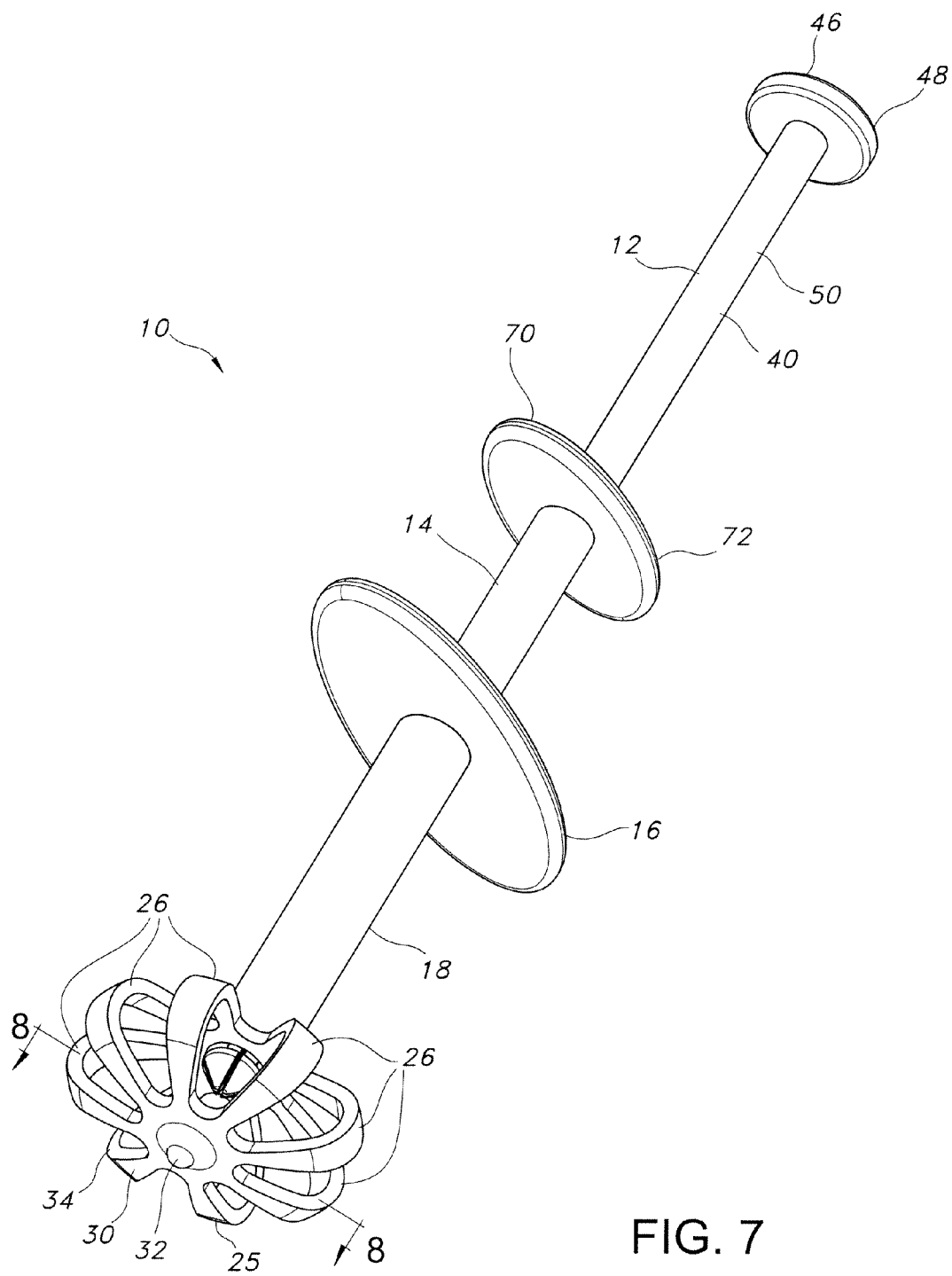
FIG. 7 is a perspective view of an exemplary enteral feeding assembly, showing the actuator positioned within the catheter and the obturator positioned within the actuator.

As illustrated in FIG. 4-6, the obturator 12 is generally, but not by way of limitation, formed as an elongated cylindrically-shaped body 40 with a distal end 42 which may be generally flat, rounded or have a configuration such that it does not present sharp edges that may cut or slice the material of the retainer and which cooperates with the detent 36 provided by the dimple 32. The obturator 12 has a proximal end 46 having a plunger handle 48 formed thereon. An outer surface 50 of the obturator 12 has diameter which is less than the diameter of the lumen 24 of the catheter 18.

Figure 9:
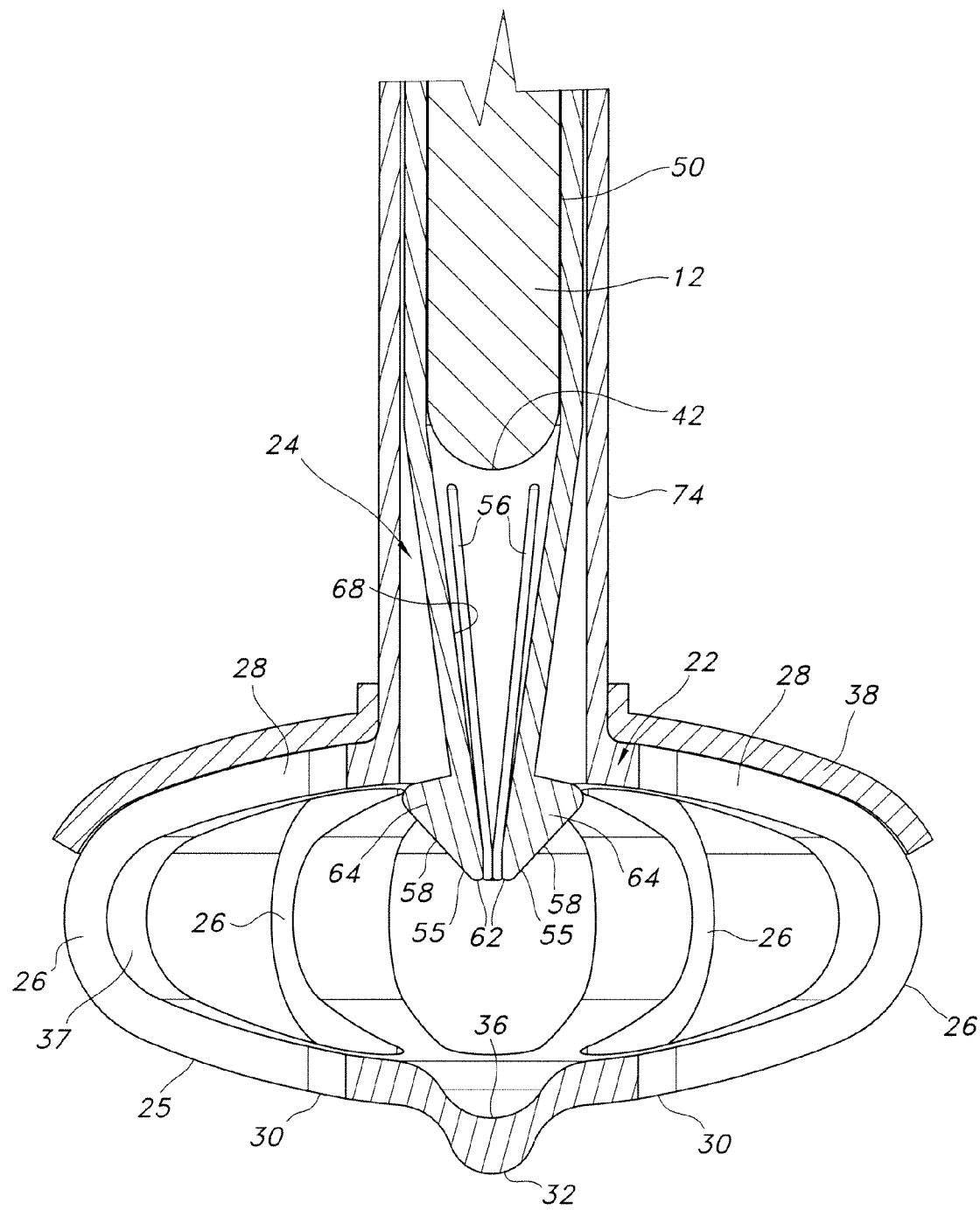
FIG. 9 is a side sectional view similar to FIG. 8, but showing a shroud positioned over and about a proximal end of a plurality of struts forming a retainer.

An actuator 14, as shown in FIGS. 3-7, is used to insert the obturator 12 into the lumen 24 defined by the walls of the catheter 18. The actuator 14 has a generally elongated hollow cylindrically-shaped body 52 and may be provided in a variety of lengths and/or sizes. As a non-limiting example, the actuator may be provided in sizes ranging from about 12 French to about 24 French. The distal end 54 of the actuator 14 is tapered inward, and it has, but not by way of limitation, two or more slits, and desirably, it has four slits 56 (FIGS. 4, 6 and 8-11). The slits 56 are desirably positioned at equal angles relative to each other and in this instance are positioned about 90 degrees from each other on the distal end 54. The slits 56 divide the distal end 54 into four end portions 55. Each end portion 55 has a catch 58 on it. Each catch 58 extends outward radially from a distal-most point 62 to provide at least one radial edge 64, as shown in FIGS. 8 and 9. The edge 64 does not extend beyond the outer diameter of the outer surface 66 of the actuator 14. The outer surface 66 of the actuator 14 has an outer diameter which is smaller than an inner diameter of the lumen 24. The actuator 14 also has an inner surface 68 which has a diameter which is configured to receive the obturator 12 therein. The actuator 14 also has a proximal end 70 having a plunger handle 72 formed thereon.

When the obturator 12 is introduced into the actuator 14, the actuator 14 is designed to permit the distal end 42 of the obturator 12 to extend to and through the end portions 55 of the distal end 62 of the actuator 14, as illustrated in FIGS. 6 and 8-11. The obturator 12 may be pre-inserted into the actuator 14 but not inserted far enough into the actuator 14 to cause movement of the distal end portions 55 of the actuator 15 prior to inserting the actuator into the catheter 18 of the enteral feeding assembly. For example, the obturator 12 and the actuator 14 may be assembled together in a manner similar to a syringe assembly so that a physician or medical professional does not need to introduce the obturator into the catheter.

Figure 2:
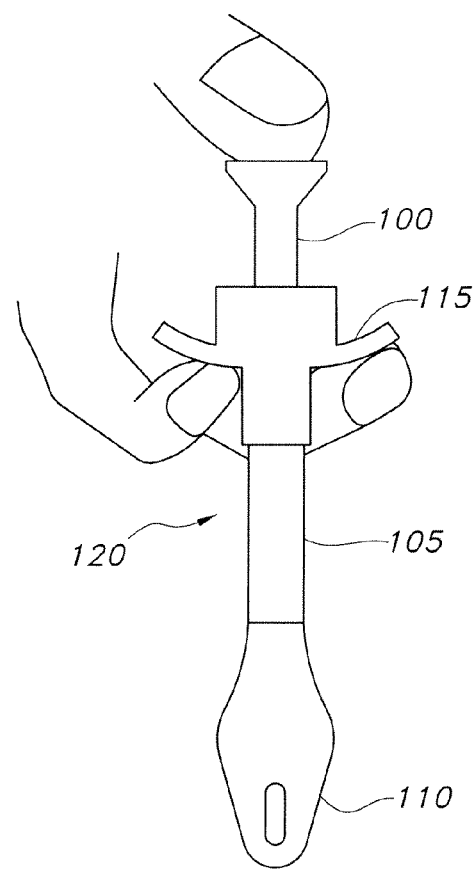
FIG. 2 is an illustration of a conventional prior art device in which a stylet is positioned in the device and force is applied to elongate the device.
Figure 3:
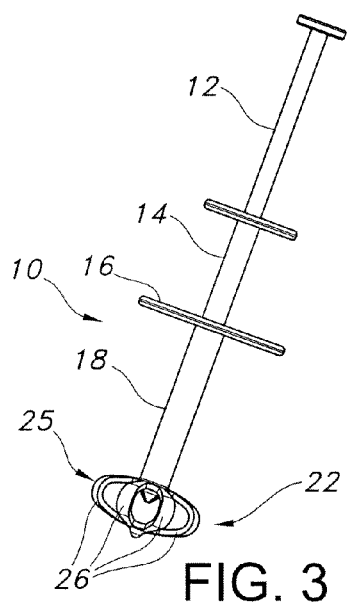
FIG. 3 is a side view of an exemplary enteral feeding assembly of the present invention, showing an actuator positioned therein and an obturator positioned within the actuator.

As the distal end 42 of the obturator 12 extends to and through the end portions 55 of the distal end 62 of the actuator 14, the slits 56 permit the inwardly tapered end portions 55 of the actuator 14 to expand radially outward. As the inwardly tapered end portions 55 expand, the edge 64 of each catch 58 is positioned to extend beyond the outer diameter of the outer surface 66 of the actuator 14. As the edge 64 of each catch 58 extends beyond the outer diameter of the outer surface 66 of the actuator 14, the edge 64 of each catch 58 engages the distal end 22 of the catheter 18. By engaging the distal end 22 of the catheter 18, the actuator 14 holds the catheter 18 in place at its distal end 18 to resist stretching force that is applied to the retainer 25. In contrast and as illustrated in FIGS. 1 and 2, conventional devices 120 are held at the base 115, and the tube 105 of the catheter is stretched along with the retainer 110. While one might consider making the tube 105 out of a non-stretchable material, using such a non-stretchable material limits the flexibility of the tube and is unsatisfactory for the comfort of the person wearing with device.

Figure 9A:
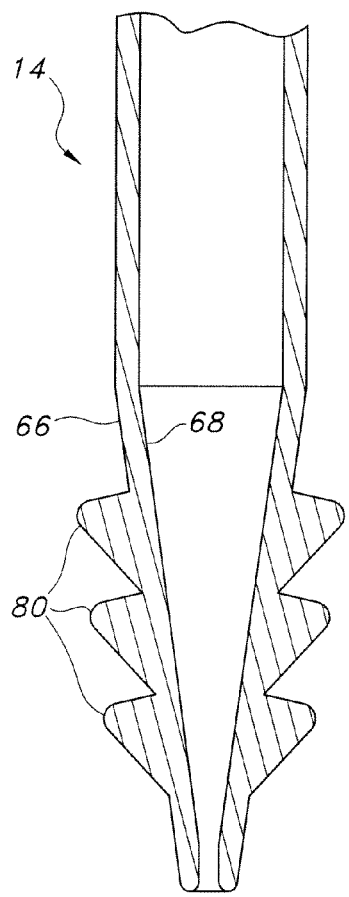
FIGS. 9A, 9B and 9C are cross-sectional side views showing an exemplary feature of an exemplary actuator.
Figure 9B:
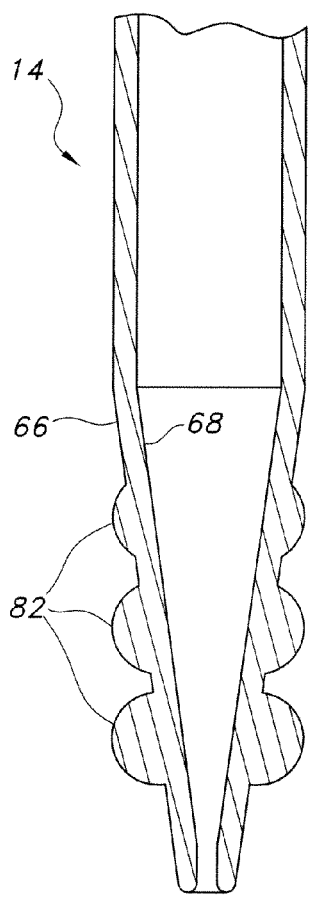
Figure 9C:
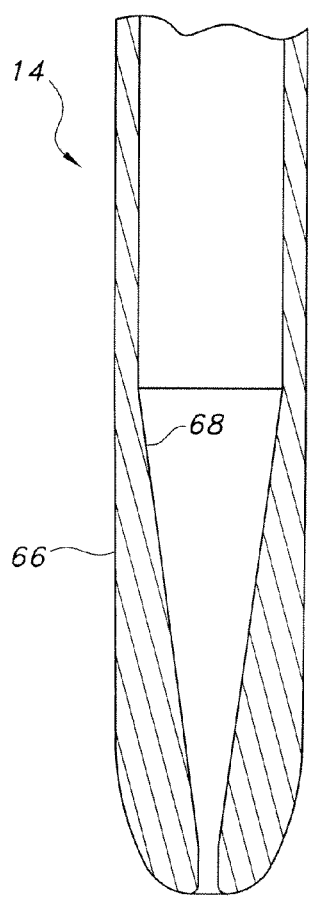

While the actuator 14 is described as employing a plurality of catches 58 to engage the distal end 22 of the catheter, the actuator may employ other mechanisms to engage the catheter in addition to the plurality of catches 58 or as an alternative to the plurality of catches. For example, the actuator 14 may utilize a plurality of barbs 80 at the outer surface 66 of the actuator as generally illustrated in cross-sectional side view in FIG. 9A in addition to the plurality of catches 58 or as an alternative to the plurality of catches 58. The barbs 80 need not have a sharp point as the expansion of the actuator when the obturator is inserted will create sufficient pressure when the barbs 80 on the outer surface 66 of the actuator 15 are urged to frictionally engage the relatively softer material of the catheter wall defining the lumen 24 of the catheter 18 to restrain the catheter 18 in a relatively fixed position. It is contemplated that other geometries such as, for example, hemispherical buds as generally illustrated in cross-sectional side view in FIG. 9B may be used in addition to the plurality of catches or as an alternative to the plurality of catches 58. The barbs 80 or hemispherical buds 82 or the like may be discrete projections from the outer surface 66 of the actuator 14 or they may span the outer surface 66 near the distal end of the actuator 14 to provide a ribbed or rippled appearance. As yet another example and as generally illustrated in cross-sectional side view in FIG. 9C, it is contemplated that outer surface 66 of the actuator 14 adjacent the distal end 54 may be relatively smooth (e.g., without catches, barbs, buds, ribs, ripples or the like) and still able to frictionally engage the wall of the catheter defining the lumen 24 by increasing the wall thickness of the actuator 14 at and/or adjacent its distal end 54 ends (i.e., by increasing the distance between the outer surface 66 of the actuator 14 and the inner surface 68 of the actuator 14) such that insertion of the obturator 12 presses against the inner surface 68 of the actuator 14 to urge the outer surface of the actuator 14 against the wall of the catheter defining the lumen 24.

In a method of use, the obturator 12 and actuator 14 are used to position a portion of the enteral feeding assembly 10 through a stoma formed in a patient and into a body lumen of the patient, such as, for example, the patient's stomach lumen (not shown). To position a portion of the catheter 18 and the retainer 25 into the body lumen, the actuator 14 is first inserted axially into the lumen 24 of the catheter 18 (FIG. 5). The distal end 54 of the actuator 14 is moved through the lumen 24 of the catheter 18 until the catch 58 on each end portion 55 of the actuator 14 are positioned just distal to the distal end 22 of the catheter 18 (FIGS. 8-11). This may be accomplished by markings on the actuator, stop(s) or ring(s) or the like at the appropriate position(s) on the actuator to match the length of the catheter. These markings may be provided for a single size of catheter or may be provided for various lengths of catheters. As a non-limiting example, the marking may be provided on a single actuator for catheter lengths ranging from 0.8 cm to about 6 cm.

The obturator 12 is then inserted into the actuator 14 until the distal end 42 of the obturator 12 extends beyond the distal end portions 55 of the actuator 14. The distal end 42 engages the detent 36 created by the dimple 32 on the inner surface 37 of the retainer 25 and moves the plurality of struts 26 from their preformed position in a radially-extending arc or arch. Of course, it is contemplated that the obturator 12 may be pre-inserted into the actuator 14 but not inserted far enough into the actuator 14 to cause movement of the distal end portions 55 of the actuator 15 prior to inserting the actuator into the catheter of the assembly.

The obturator 12 moves the plurality of struts 26 distally so that they align axially against the outer surface 50 of the obturator 12 (FIGS. 11 and 12). Simultaneously, it will be understood that the shroud 38 follows the plurality of struts 26 into this axial alignment, such that the shroud 38 (which may include axially positioned folds) also is in an axial alignment as well (not shown). The shroud 38 may be integrally formed with the struts 26 or may be separately attached to the struts 26. That is, the shroud 38 may be in the form of a web extending between the struts 26 where the struts 26 are joined to the catheter 18.

Figure 10:
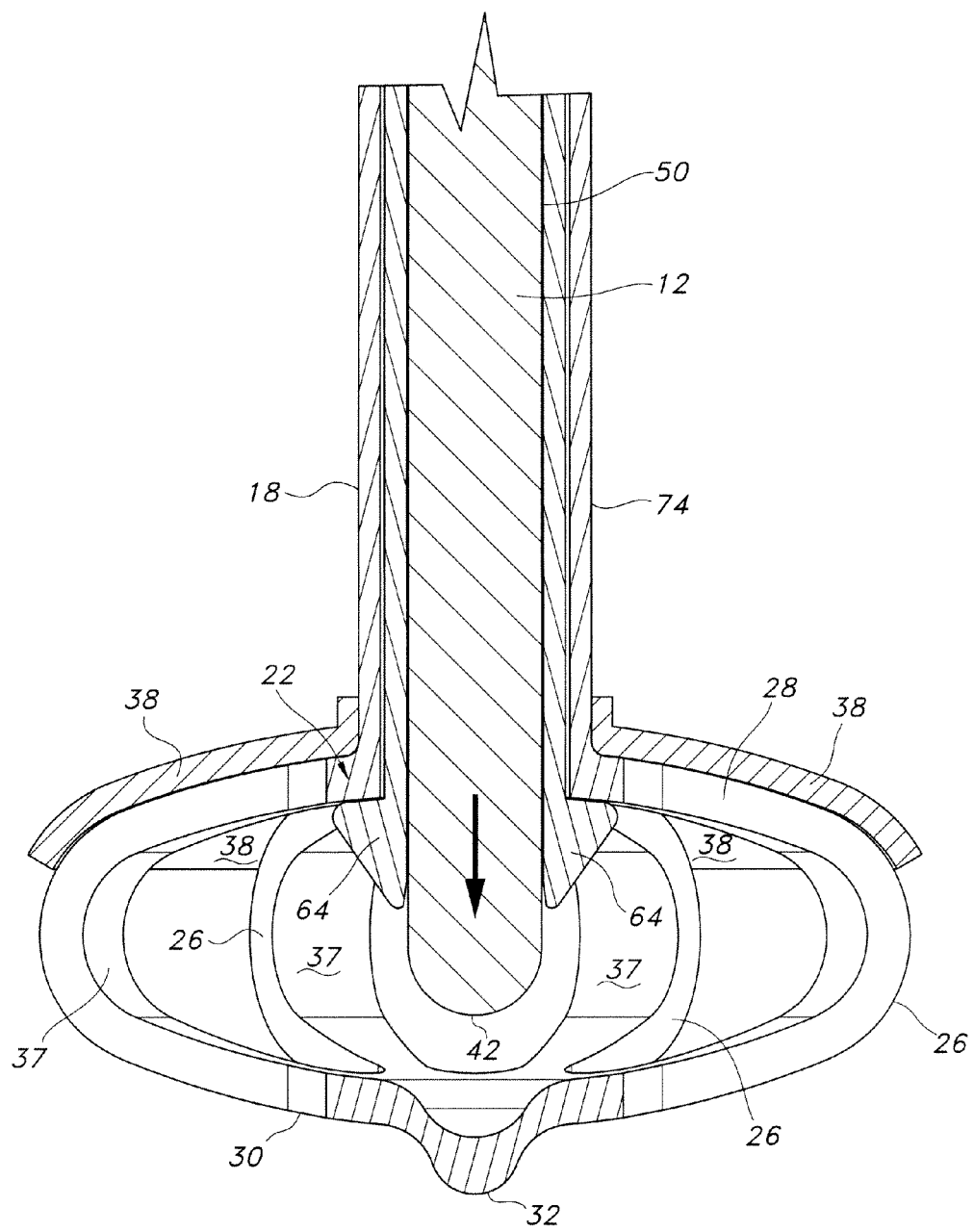
FIG. 10 is a side view of an exemplary enteral feeding assembly showing the obturator extending through the actuator such that the catches on the distal end of the actuator engage a catheter of the enteral feeding assembly.

To move the plurality of struts 26 and the shroud 38, a user depresses the plunger handle 48 of the obturator 12 until it is positioned against or near the plunger handle 72 of the actuator 14. For example, force may be applied to the plunger handle 48 of the obturator 12 by grasping the plunger handle 72 at the proximal end 70 of the actuator 14 with the index finger and middle finger and by pressing the obturator plunger head 48 down with a thumb in an action similar to applying pressure to the plunger of a syringe as generally illustrated in FIG. 8A. Of course, other configurations for grasping or holding and applying force are contemplated. Importantly, force is not applied to the catheter tube itself. Instead, elongation force is applied only to the retainer 25 at and beyond the distal end 22 of the catheter 18. More specifically, force is applied as the distal end 42 of the obturator 12 contacts and urges the dimple 32 and surrounding structure formed at the junction formed at the distal ends 30 of the plurality of struts 26 generally along the longitudinal axis away from the distal end 22 of the catheter 18 while the catheter 18 itself remains in a stationary position relative to the obturator 12 and the actuator 14 because each catch 58 on each end portion 55 of the actuator 14 engage the distal end 22 of the catheter 18 as generally shown in FIGS. 10 and 11.

As the distal end 42 of the obturator 12 contacts the dimple 32 at the junction formed at the distal ends 30 of the plurality of struts 26 and the plurality of catches 58 hold the distal end 22 of the catheter 18 and the enteral feeding assembly 10 in a stationary position relative to the actuator 14, the plunger handle 72 of the actuator 14 may provide guidance to a user as to how far to push the obturator 12. That is, the actuator 14 and the obturator 12 may be designed so that when a user moves the plunger handle 48 of the obturator 12 against or next to the plunger handle 72 of the actuator 14, the obturator 12 travels a sufficient distance to move the plurality of struts 26 (and shroud 28—if present) into the desired axial position relative to the distal end 22 of the catheter 18 (FIGS. 11 and 12). When this occurs, the plurality of struts 26 are moved into an axially-aligned position next to the outer surface 50 of the obturator 12. If a shroud is utilized, the shroud is moved into an axially aligned position next to the outer surface 34 of the plurality of struts 26 (not shown). This position provides a diameter of the combination of the obturator 12, and plurality of struts 26, (and shroud 38—if present) which is similar to a diameter of an outer surface 74 of the catheter 18. This configuration reduced trauma to both the stoma and the body lumen during placement of the enteral feeding assembly 10. In this manner, the retainer 25 and a substantial portion of the catheter 18 is moved through the stoma until the retainer 25 is positioned within the patient's body lumen (not shown).

Once the retainer 25 is in the body lumen, the obturator 12 is slowly withdrawn, thereby permitting the plurality of struts 26 to return to their preformed position, forming a radial arc or arch which collectively forms the sphere-like structure of the retainer 25 (FIGS. 3-10). Similarly, if a shroud 38 is present, the shroud 38 expands and forms a hemispherical-like shape over a proximal portion of the plurality of struts 26 (FIG. 9). When the obturator 12 is withdrawn, the distal end 54 of the actuator 14 returns to its inwardly tapered configuration (FIG. 9). This configuration moves each distal end portions 55 and each catch 58 thereon inward radially and away from the lumen 24 of the distal end 22 of the catheter 18. This action of the distal end 54 reduces an outer diameter of the distal end 55 to less than the diameter of the lumen 24 of the catheter 18. The actuator 14 is then withdrawn from the lumen 24 of the catheter 18. It will be appreciated that the method described above would be repeated in order to remove the enteral feeding assembly 10 from a body lumen.

The enteric feeding assembly and the obturator and actuator may be formed from any material or combination of materials which permit the assembly 10, obturator 12 and/or actuator 14 to operate as shown and/or described herein. Similarly, all shapes and configurations shown and/or described herein are only as examples and are intended as non-limiting. Any shape(s) and/or configuration(s) may be utilized, so long as the device(s) describes operates as illustrated and/or described herein.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An enteral feeding assembly, comprising:
 a base, the base defining an opening therethrough;
 a flexible catheter having a proximal end and a distal end, a longitudinal axis, width and a length; the catheter being positioned through the base in communication with the opening therein, a portion of the catheter extending away from the base to define the distal end, the catheter having walls defining a catheter lumen from the opening defined in the base to the distal end of the catheter;
 a retainer provided on the distal end of the catheter, the retainer having:
 a proximal end and a distal end and a longitudinal axis,
 a plurality of struts having a flexible, preformed configuration which cooperate to form at least a portion of a retainer shape about the longitudinal axis with openings between the struts and a flexible shroud positioned over or incorporated with at least a portion of the struts at the proximal end of the retainer to prevent the struts from causing irritation or embedding in a body lumen;
 an actuator configured to fit through the opening defined by the base and to fit within the lumen of the flexible catheter, a distal end of the actuator including two or more slits that divide the distal end of the actuator into end portions, each end portion further including a catch extending outwards radially to provide at least one radial edge; and
 an obturator that is configured to fit within the actuator;
 wherein the actuator and obturator combination is configured to alternate the retainer between: (a) an insertion configuration that is generated by applying an elongating force generally along the longitudinal axis of the retainer such that the struts and the shroud of the retainer are substantially axially aligned with the catheter to an insertion width that is substantially the same as the catheter width and an insertion length, and (b) a deployed configuration in the absence of the elongating force in which the struts and the shroud of the retainer have a deployed width that is substantially greater than the width of the catheter and a deployed length that is less than insertion length, and wherein the obturator and the actuator are configured to engage a distal end of the catheter so that an elongating force may be applied along the longitudinal axis of the retainer to move the retainer from a deployed configuration to an insertion configuration such that the length of the flexible catheter is not significantly altered when the retainer is alternated between such configurations.

2. The enteral feeding assembly of claim 1, wherein the retainer shape is a generally spherical shape.

3. The enteral feeding assembly of claim 1, wherein the flexible shroud and the proximal portions of the struts are a monolithic structure.

4. The enteral feeding assembly of claim 1, wherein an outer surface of the actuator adjacent a distal end of the actuator further includes projections from the outer surface configured to engage the walls of the flexible catheter defining the catheter lumen.

5. A method of positioning at least a portion of an enteral feeding assembly in a body lumen, the method comprising:
 positioning the enteral feeding assembly of claim 1 near a stoma to a body lumen,
 inserting an actuator into the catheter lumen of the assembly, the actuator having a plunger handle at a proximal end and a split distal end including end portions, each end portion including at least one catch thereon, the distal end tapered and configured to have a diameter smaller than a diameter of the catheter lumen,
 moving the distal end of the actuator such that the end portions extend through the distal end of the catheter such that the catch on each end portion is positioned against a portion of the distal end of the catheter;
 inserting an obturator having a distal end and a plunger handle on a proximal end into the actuator such that the obturator extends beyond the actuator and is positioned against at least a portion of the plurality of struts,
 moving the obturator handle next to the actuator handle to apply an elongating force generally along the longitudinal axis of the retainer to move the retainer to the insertion configuration;
 inserting the retainer and at least a portion of the catheter into the stoma until the retainer is positioned within the body lumen;

removing the obturator, thereby removing the elongating force and permitting the retainer to move to the deployed configuration within the body lumen; and removing the actuator from the catheter.

6. The method of claim 5 wherein the obturator is pre-inserted into the actuator but not inserted far enough into the actuator to cause movement of the distal end of the actuator prior to inserting the actuator into the catheter of the assembly.

7. An enteral feeding assembly, comprising:

a base, the base defining an opening therethrough;

a flexible catheter having a proximal end and a distal end, a longitudinal axis, width and a length; the catheter being positioned through the base in communication with the opening therein, a portion of the catheter extending away from the base to define the distal end, the catheter having walls defining a catheter lumen from the opening defined in the base to the distal end of the catheter;

a retainer provided on the distal end of the catheter, the retainer having:

a proximal end and a distal end and a longitudinal axis, a plurality of struts having a flexible, preformed configuration which cooperate to form at least a portion of a retainer shape about the longitudinal axis with openings between the struts and a flexible shroud positioned over or incorporated with at least a portion of the struts at the proximal end of the retainer to prevent the struts from causing irritation or embedding in a body lumen;

an actuator configured to fit through the opening defined by the base and to fit within the lumen of the flexible catheter, a distal end of the actuator including two or more slits that divide the distal end of the actuator into end portions, each end portion further including a catch extending outwards radially to provide at least one radial edge configured to engage the distal end of the flexible catheter; and an obturator that is configured to fit within the actuator, the actuator and obturator configured for applying an elongating force along the longitudinal axis of the retainer to move the retainer from a deployed configuration to an insertion configuration, wherein the retainer may be alternated between: (a) an insertion configuration that is generated by applying an elongating force generally along the longitudinal axis of the retainer such that the struts and the shroud of the retainer are substantially axially aligned with the catheter to an insertion width that is substantially the same as the catheter width and an insertion length, and (b) a deployed configuration in the absence of the elongating force in which the struts and the shroud of the retainer have a deployed width that is substantially greater than the width of the catheter and a deployed length that is less than insertion length, and wherein the obturator and the actuator are configured to engage a distal end of the catheter and the walls of the flexible catheter defining the catheter lumen so that an elongating force may be applied along the longitudinal axis of the retainer to move the retainer from a deployed configuration to an insertion configuration such that the length of the flexible catheter is not significantly altered when the retainer is alternated between such configurations.

8. The enteral feeding assembly of claim 7, wherein an outer surface of the actuator adjacent a distal end of the actuator includes projections from the outer surface configured to engage the walls of the flexible catheter defining the catheter lumen.

9. The enteral feeding assembly of claim 7, wherein the retainer shape is a generally spherical shape.

10. The enteral feeding assembly of claim 7, wherein the flexible shroud and the proximal portions of the struts are a monolithic structure.

* * * * *